(12) United States Patent
Nguyen et al.

(10) Patent No.: US 11,759,317 B2
(45) Date of Patent: *Sep. 19, 2023

(54) THREE-DIMENSIONAL WOVEN FABRIC IMPLANT DEVICES

(71) Applicant: Edwards Lifesciences Corporation, Irvine, CA (US)

(72) Inventors: Son V. Nguyen, Irvine, CA (US); Kevin D. Rupp, Irvine, CA (US); Ajay Chadha, Irvine, CA (US); Jeff Lindstrom, Coto de Caza, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 294 days.

This patent is subject to a terminal disclaimer.

(21) Appl. No.: 17/071,641

(22) Filed: Oct. 15, 2020

(65) Prior Publication Data

US 2021/0022852 A1 Jan. 28, 2021

Related U.S. Application Data

(63) Continuation of application No. 15/841,046, filed on Dec. 13, 2017, now Pat. No. 10,813,749.

(60) Provisional application No. 62/436,866, filed on Dec. 20, 2016.

(51) Int. Cl.
*A61F 2/24* (2006.01)
*D03D 3/02* (2006.01)
*D03D 25/00* (2006.01)
*D03D 15/283* (2021.01)

(52) U.S. Cl.
CPC ............. *A61F 2/2409* (2013.01); *D03D 3/02* (2013.01); *D03D 15/283* (2021.01); *D03D 25/005* (2013.01); *A61F 2/2418* (2013.01); *A61F 2210/0019* (2013.01); *A61F 2210/0071* (2013.01); *A61F 2210/0076* (2013.01); *A61F 2220/0075* (2013.01); *A61F 2230/0069* (2013.01); *A61F 2240/004* (2013.01); *A61F 2250/006* (2013.01); *A61F 2250/0069* (2013.01); *D10B 2509/00* (2013.01)

(58) Field of Classification Search
CPC ........ A61F 2/24; A61F 2/2409; A61F 2/2418; A61F 2210/0071; A61F 2210/0076; A61F 2220/0075; A61F 2230/0069; A61F 2240/004; A61F 2250/006; A61F 2250/0069
See application file for complete search history.

(56) References Cited

U.S. PATENT DOCUMENTS

| 1,392,535 A | 10/1921 | Stevenson |
| 3,365,728 A | 1/1968 | Edwards et al. |
| 3,725,961 A | 4/1973 | Magovern et al. |

(Continued)

FOREIGN PATENT DOCUMENTS

| AU | 2002212418 B2 | 3/2006 |
| CN | 1182813 A | 5/1998 |

(Continued)

*Primary Examiner* — Paul B Prebilic
(74) *Attorney, Agent, or Firm* — Alan T. Hale; Chang & Hale, LLP

(57) ABSTRACT

A docking device includes a hollow cylindrical body portion having an internal surface and an outer surface. The hollow cylindrical body portion is formed of a three-dimensional (3D) woven fabric comprising a plurality of different types of fibers.

22 Claims, 5 Drawing Sheets

(56) References Cited

U.S. PATENT DOCUMENTS

| | | | |
|---|---|---|---|
| 3,983,581 A | 10/1976 | Angell et al. | |
| 4,035,849 A | 7/1977 | Angell et al. | |
| 4,182,618 A | 1/1980 | Tschudy | |
| 4,187,618 A * | 2/1980 | Diehl | D21F 7/083 |
| | | | 442/271 |
| 5,059,177 A | 10/1991 | Towne et al. | |
| 5,258,023 A | 11/1993 | Reger | |
| 5,399,418 A * | 3/1995 | Hartmanns | B64G 6/00 |
| | | | 442/205 |
| 5,411,552 A | 5/1995 | Andersen et al. | |
| 5,476,506 A | 12/1995 | Lunn | |
| 5,554,185 A | 9/1996 | Block et al. | |
| 5,628,786 A | 5/1997 | Banas et al. | |
| 5,693,088 A | 12/1997 | Lazarus | |
| 5,711,960 A | 1/1998 | Shikinami | |
| 5,755,783 A | 5/1998 | Stobie et al. | |
| 5,769,882 A | 6/1998 | Fogarty et al. | |
| 5,776,188 A | 7/1998 | Shepherd et al. | |
| 5,840,081 A | 11/1998 | Andersen et al. | |
| 5,843,161 A | 12/1998 | Solovay | |
| 5,843,179 A | 12/1998 | Vanney et al. | |
| 5,855,601 A | 1/1999 | Bessler et al. | |
| 5,957,949 A | 9/1999 | Leonhardt et al. | |
| 6,015,431 A | 1/2000 | Thornton et al. | |
| 6,110,198 A | 8/2000 | Fogarty et al. | |
| 6,168,614 B1 | 1/2001 | Andersen et al. | |
| 6,206,911 B1 | 3/2001 | Milo | |
| 6,306,164 B1 | 10/2001 | Kujawski | |
| 6,352,554 B2 | 3/2002 | De Paulis | |
| 6,419,696 B1 | 7/2002 | Ortiz et al. | |
| 6,432,134 B1 | 8/2002 | Anson et al. | |
| 6,458,153 B1 | 10/2002 | Bailey et al. | |
| 6,482,228 B1 | 11/2002 | Norred | |
| 6,527,979 B2 | 3/2003 | Constantz et al. | |
| 6,540,782 B1 | 4/2003 | Snyders | |
| 6,582,462 B1 | 6/2003 | Andersen et al. | |
| 6,652,578 B2 | 11/2003 | Bailey et al. | |
| 6,663,667 B2 | 12/2003 | Dehdashtian et al. | |
| 6,689,162 B1 | 2/2004 | Thompson | |
| 6,729,356 B1 | 5/2004 | Baker et al. | |
| 6,730,121 B2 | 5/2004 | Ortiz et al. | |
| 6,773,456 B1 | 8/2004 | Gordon et al. | |
| 6,797,002 B2 | 9/2004 | Spence et al. | |
| 6,814,754 B2 | 11/2004 | Greenhalgh | |
| 6,846,325 B2 | 1/2005 | Liddicoat | |
| 6,904,909 B2 | 6/2005 | Andreas et al. | |
| 6,908,481 B2 | 6/2005 | Cribier | |
| 6,911,040 B2 | 6/2005 | Johnson et al. | |
| 7,018,406 B2 | 3/2006 | Seguin et al. | |
| 7,018,408 B2 | 3/2006 | Bailey et al. | |
| 7,037,334 B1 | 5/2006 | Hlavka et al. | |
| 7,077,861 B2 | 7/2006 | Spence | |
| 7,101,395 B2 | 9/2006 | Tremulis et al. | |
| 7,101,396 B2 | 9/2006 | Artof et al. | |
| 7,125,421 B2 | 10/2006 | Tremulis et al. | |
| 7,147,663 B1 | 12/2006 | Berg et al. | |
| 7,175,652 B2 | 2/2007 | Cook et al. | |
| 7,192,441 B2 | 3/2007 | Sherry | |
| 7,264,632 B2 | 9/2007 | Wright et al. | |
| 7,585,321 B2 | 9/2009 | Cribier | |
| 7,618,446 B2 | 11/2009 | Andersen et al. | |
| 7,731,742 B2 | 6/2010 | Schlick et al. | |
| 7,737,060 B2 | 6/2010 | Strickler et al. | |
| 7,780,725 B2 | 8/2010 | Haug et al. | |
| 7,785,366 B2 | 8/2010 | Maurer et al. | |
| 7,951,195 B2 | 5/2011 | Antonsson et al. | |
| 8,105,377 B2 | 1/2012 | Liddicoat | |
| 8,128,681 B2 | 3/2012 | Shoemaker et al. | |
| 8,323,335 B2 | 12/2012 | Rowe et al. | |
| 8,377,115 B2 | 2/2013 | Thompson | |
| 8,398,708 B2 | 3/2013 | Meiri et al. | |
| 8,425,593 B2 | 4/2013 | Braido et al. | |
| 8,430,925 B2 | 4/2013 | Forster et al. | |
| 8,449,605 B2 | 5/2013 | Lichtenstein et al. | |
| 8,449,606 B2 | 5/2013 | Eliasen et al. | |
| 8,657,872 B2 | 2/2014 | Seguin | |
| 8,663,322 B2 | 3/2014 | Keranen | |
| 8,672,998 B2 | 3/2014 | Lichtenstein et al. | |
| 8,721,717 B2 | 5/2014 | Shoemaker et al. | |
| 8,734,507 B2 | 5/2014 | Keranen | |
| 8,795,357 B2 | 8/2014 | Yohanan et al. | |
| 8,808,356 B2 | 8/2014 | Braido et al. | |
| 8,845,721 B2 | 9/2014 | Braido et al. | |
| 8,940,041 B2 | 1/2015 | Carlson et al. | |
| 8,979,922 B2 | 3/2015 | Jayasinghe et al. | |
| 8,992,608 B2 | 3/2015 | Haug et al. | |
| 9,078,747 B2 | 7/2015 | Conklin | |
| 9,095,434 B2 | 8/2015 | Rowe | |
| 9,119,718 B2 | 9/2015 | Keranen | |
| 9,220,594 B2 | 12/2015 | Braido et al. | |
| 9,237,886 B2 | 1/2016 | Seguin et al. | |
| 9,241,794 B2 | 1/2016 | Braido et al. | |
| 9,289,296 B2 | 3/2016 | Braido et al. | |
| 9,326,856 B2 | 5/2016 | Schraut et al. | |
| 9,345,571 B1 | 5/2016 | Braido et al. | |
| 9,351,828 B2 | 5/2016 | Braido et al. | |
| 9,351,831 B2 | 5/2016 | Braido et al. | |
| 9,351,832 B2 | 5/2016 | Braido et al. | |
| 9,364,326 B2 | 6/2016 | Yaron | |
| 9,414,911 B2 | 8/2016 | Braido et al. | |
| 9,463,268 B2 | 10/2016 | Spence | |
| 9,474,599 B2 | 10/2016 | Keranen | |
| 9,545,307 B2 | 1/2017 | Braido et al. | |
| 9,549,815 B2 | 1/2017 | Braido et al. | |
| 9,622,863 B2 | 4/2017 | Karapetian et al. | |
| 2001/0021872 A1 | 9/2001 | Bailey et al. | |
| 2001/0027338 A1 | 10/2001 | Greenberg | |
| 2001/0039450 A1 | 11/2001 | Pavcnik et al. | |
| 2003/0074058 A1 | 4/2003 | Sherry | |
| 2003/0225420 A1 | 12/2003 | Wardle | |
| 2003/0236567 A1 | 12/2003 | Elliot | |
| 2004/0033364 A1 | 2/2004 | Spiridigliozzi et al. | |
| 2004/0082989 A1 | 4/2004 | Cook et al. | |
| 2004/0098096 A1 | 5/2004 | Eton | |
| 2004/0210304 A1 | 10/2004 | Seguin et al. | |
| 2004/0215320 A1 | 10/2004 | Machek | |
| 2004/0260389 A1 | 12/2004 | Case et al. | |
| 2005/0043790 A1 | 2/2005 | Seguin | |
| 2005/0096736 A1 | 5/2005 | Osse et al. | |
| 2005/0119735 A1 | 6/2005 | Spence et al. | |
| 2005/0137687 A1 | 6/2005 | Salahieh et al. | |
| 2005/0137691 A1 | 6/2005 | Salahieh et al. | |
| 2005/0203614 A1 | 9/2005 | Forster et al. | |
| 2005/0203617 A1 | 9/2005 | Forster et al. | |
| 2006/0025857 A1 | 2/2006 | Bergheim et al. | |
| 2006/0089672 A1 | 4/2006 | Martinek | |
| 2007/0073387 A1 | 3/2007 | Forster et al. | |
| 2007/0203575 A1 | 8/2007 | Forster et al. | |
| 2007/0265700 A1 | 11/2007 | Eliasen et al. | |
| 2007/0293927 A1 | 12/2007 | Frank et al. | |
| 2008/0033542 A1 | 2/2008 | Antonsson et al. | |
| 2008/0125853 A1 | 5/2008 | Bailey et al. | |
| 2008/0208330 A1 | 8/2008 | Keranen | |
| 2009/0099653 A1 | 4/2009 | Suri et al. | |
| 2009/0132035 A1 | 5/2009 | Roth et al. | |
| 2010/0145440 A1 | 6/2010 | Keranen | |
| 2010/0168839 A1 | 7/2010 | Braido et al. | |
| 2010/0312333 A1 | 12/2010 | Navia et al. | |
| 2010/0318184 A1 | 12/2010 | Spence | |
| 2012/0035719 A1 | 2/2012 | Forster et al. | |
| 2012/0059458 A1 | 3/2012 | Buchbinder et al. | |
| 2012/0116492 A1 | 5/2012 | Seibold et al. | |
| 2012/0215303 A1 | 8/2012 | Quadri et al. | |
| 2013/0006279 A1 | 1/2013 | Mortarino | |
| 2013/0273795 A1 | 10/2013 | Richter | |
| 2013/0331929 A1 | 12/2013 | Mitra et al. | |
| 2013/0338765 A1 | 12/2013 | Braido et al. | |
| 2014/0074299 A1 | 3/2014 | Endou et al. | |
| 2014/0172070 A1 | 6/2014 | Seguin | |
| 2014/0243966 A1 | 8/2014 | Garde et al. | |
| 2014/0277424 A1 | 9/2014 | Oslund | |
| 2014/0303719 A1 | 10/2014 | Cox et al. | |
| 2014/0350663 A1 | 11/2014 | Braido et al. | |
| 2014/0379074 A1 | 12/2014 | Spence et al. | |

(56) References Cited

U.S. PATENT DOCUMENTS

| | | | |
|---|---|---|---|
| 2015/0073541 A1 | 3/2015 | Salahieh et al. | |
| 2015/0073546 A1 | 3/2015 | Braido | |
| 2015/0127088 A1 | 5/2015 | Carlson et al. | |
| 2015/0157455 A1 | 6/2015 | Hoang et al. | |
| 2015/0190552 A1 | 7/2015 | Richter | |
| 2015/0230921 A1 | 8/2015 | Chau et al. | |
| 2015/0230953 A1 | 8/2015 | Bar et al. | |
| 2015/0282931 A1 | 10/2015 | Brunnett et al. | |
| 2015/0282932 A1 | 10/2015 | Neuman et al. | |
| 2015/0327999 A1 | 11/2015 | Board et al. | |
| 2015/0335428 A1 | 11/2015 | Keranen | |
| 2015/0374493 A1 | 12/2015 | Yaron et al. | |
| 2016/0074165 A1 | 3/2016 | Spence et al. | |
| 2016/0095705 A1 | 4/2016 | Keranen et al. | |
| 2016/0184095 A1 | 6/2016 | Spence et al. | |
| 2016/0199177 A1 | 7/2016 | Spence et al. | |
| 2016/0213466 A1 | 7/2016 | Braido et al. | |
| 2016/0213468 A1 | 7/2016 | Braido et al. | |
| 2016/0242904 A1 | 8/2016 | Braido et al. | |
| 2016/0256276 A1 | 9/2016 | Yaron | |
| 2017/0007399 A1 | 1/2017 | Keranen | |
| 2017/0007402 A1 | 1/2017 | Zerkowski et al. | |
| 2017/0172736 A1* | 6/2017 | Chadha | A61L 27/56 |
| 2019/0226126 A1* | 7/2019 | Hozumi | D03D 15/217 |

FOREIGN PATENT DOCUMENTS

| | | |
|---|---|---|
| CN | 104786564 A | 7/2015 |
| DE | 19532846 A1 | 3/1997 |
| DE | 19907646 A1 | 8/2000 |
| EP | 0592410 B1 | 10/1995 |
| EP | 0850607 A2 | 7/1998 |
| EP | 1432369 | 6/2004 |
| EP | 1521550 A2 | 4/2005 |
| EP | 2155114 A1 | 2/2010 |
| EP | 1827314 B1 | 12/2010 |
| EP | 2299938 A2 | 3/2011 |
| EP | 2620125 A1 | 7/2013 |
| EP | 2572676 A3 | 8/2013 |
| EP | 2572675 A3 | 9/2013 |
| EP | 2698129 A1 | 2/2014 |
| EP | 2726018 | 5/2014 |
| EP | 2745805 A1 | 6/2014 |
| EP | 2749254 A1 | 7/2014 |
| EP | 2806829 A2 | 12/2014 |
| EP | 2815723 A1 | 12/2014 |
| EP | 2815725 A1 | 12/2014 |
| EP | 2967851 A2 | 1/2016 |
| EP | 2926766 B1 | 2/2016 |
| EP | 2815724 B1 | 6/2016 |
| EP | 3028670 A1 | 6/2016 |
| EP | 3028671 A1 | 6/2016 |
| EP | 3025680 B1 | 2/2017 |
| EP | 3025681 B1 | 2/2017 |
| WO | 9117720 A1 | 11/1991 |
| WO | 9829057 A1 | 7/1998 |
| WO | 9748350 A8 | 6/1999 |
| WO | 0044313 A1 | 8/2000 |
| WO | 0106959 A1 | 2/2001 |
| WO | 0149213 A2 | 7/2001 |
| WO | 0154625 A1 | 8/2001 |
| WO | 0219951 A1 | 3/2002 |
| WO | 0236048 A1 | 5/2002 |
| WO | 0247575 A2 | 6/2002 |
| WO | 03047468 | 6/2003 |
| WO | 03037222 A3 | 10/2003 |
| WO | 03088873 A1 | 10/2003 |
| WO | 03096932 A1 | 11/2003 |
| WO | 03003949 A3 | 1/2004 |
| WO | 2005084595 A1 | 9/2005 |
| WO | 2006005015 A2 | 1/2006 |
| WO | 2006011127 A2 | 2/2006 |
| WO | 2005102015 A3 | 4/2007 |
| WO | 2007067942 A1 | 6/2007 |
| WO | 2009042196 A2 | 4/2009 |
| WO | 2010121076 A2 | 10/2010 |
| WO | 2013033791 A1 | 3/2013 |
| WO | 2013110722 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |

* cited by examiner

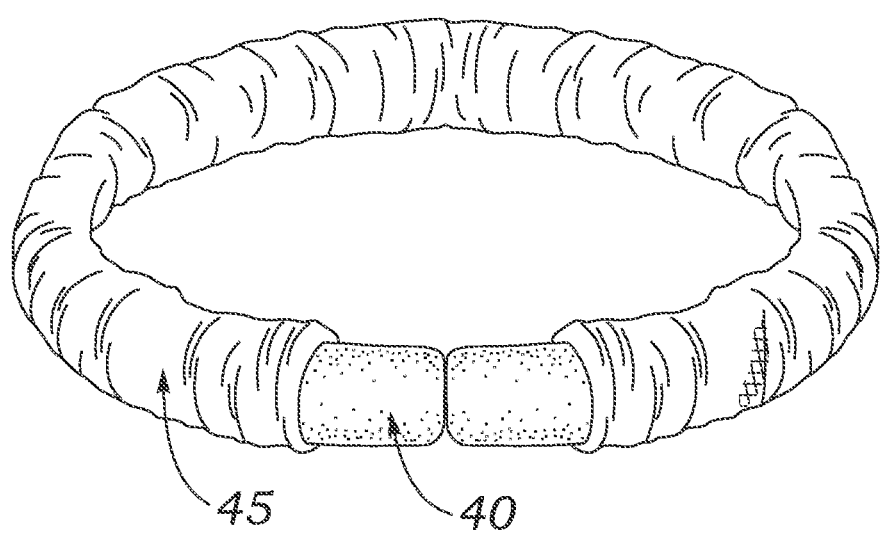

US 11,759,317 B2

THREE-DIMENSIONAL WOVEN FABRIC IMPLANT DEVICES

CROSS-REFERENCE TO RELATED APPLICATION(S)

This application is a continuation of U.S. patent application Ser. No. 15/841,046, filed on Dec. 13, 2017 and entitled DOCKING DEVICE MADE WITH 3D WOVEN FABRIC, now U.S. Pat. No. 10,813,749, which claims priority to U.S. Provisional Application No. 62/436,866, filed on Dec. 20, 2016 and entitled DOCKING DEVICE MADE WITH 3D WOVEN FABRIC, the disclosures of which are hereby incorporated by reference in their entirety.

FIELD OF THE INVENTION

This invention relates generally to docking devices for bioprostheses, including implantable bioprosthetic heart valves.

BACKGROUND

The unique geometry and sometimes irregular size of a patient's native heart valve anatomy present challenges to providing an implantable bioprosthetic heart valve that fits within and is provided in intimate contact or seal with the surrounding tissue.

SUMMARY

The present disclosure generally relates to docking devices for bioprostheses, such as bioprosthetic heart valves, and, more particularly, to docking devices that include a three-dimensional (3D) woven fabric, and methods of making such docking devices.

In some implementations, the present disclosure relates to a docking device for a bioprosthesis comprising a 3D woven fabric forming a shaped element having an internal surface, an outer surface, and a thickness therebetween, and a filler structure coupled to the outer surface of the shaped element. The bioprosthesis can be a heart valve.

In certain embodiments, the 3D woven fabric comprises first, second, and third different types of fibers or yarns. For example, the first type of fiber or yarn can comprise a shape memory material, the second type of fiber or yarn can comprise a low-melt thermoplastic polymer or resin, and the third type of fiber or yarn can comprise a high-tenacity biocompatible material. In certain embodiments, the shape memory material comprises Nitinol. In certain embodiments, the low-melt thermoplastic polymer or resin has a melting point between 85 degrees Celsius and 200 degrees Celsius. For example, the low-melt thermoplastic polymer or resin can comprise Nylon. In certain embodiments, the high-tenacity biocompatible material comprises polyethylene terephthalate (PET).

The filler structure can be covered with a material having low porosity and reduced permeability. In certain embodiments, the filler structure comprises polymer foam. For example, the polymer foam can be at least partially covered with a tubular woven fabric. In certain embodiments, the tubular woven fabric comprises PET.

In some implementations, the present disclosure relates to a 3D woven fabric for a bioprosthesis docking device comprising a shape memory material, a low-melt thermoplastic polymer or resin, and a high-tenacity biocompatible material. The shape memory material can comprise Nitinol. In certain embodiments, the low-melt thermoplastic polymer or resin has a melting point of 85 degrees Celsius to 200 degrees Celsius. The low-melt thermoplastic polymer or resin can comprise Nylon. The high-tenacity biocompatible material can comprise PET.

In some implementations, the present disclosure relates to a method for making a docking device for a bioprosthesis. The method comprises weaving a 3D woven fabric by interlacing a shape memory material, a low-melt thermoplastic polymer or resin, and a high-tenacity biocompatible material, and pressing and heating the 3D woven fabric over a shape-setting mold at temperatures greater than a melting point of the low-melt thermoplastic polymer or resin. In certain embodiments, the shape memory material comprises Nitinol, the low-melt thermoplastic polymer or resin comprises Nylon having a melting point of 85 degrees Celsius to 200 degrees Celsius, and the high-tenacity biocompatible material comprises polyethylene terephthalate (PET).

The method can further comprise attaching a filler structure to a surface of the 3D woven fabric. For example, attaching the filler structure can comprise sewing the filler structure to the surface of the 3D woven fabric. The method can further comprise covering the filler structure with a tubular woven fabric comprising PET, wherein the filler comprises polymer foam.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIG. 4 is a cutaway perspective view of a tubular woven fabric covering a polymeric foam in accordance with one or more embodiments.

DETAILED DESCRIPTION

Figure 1:
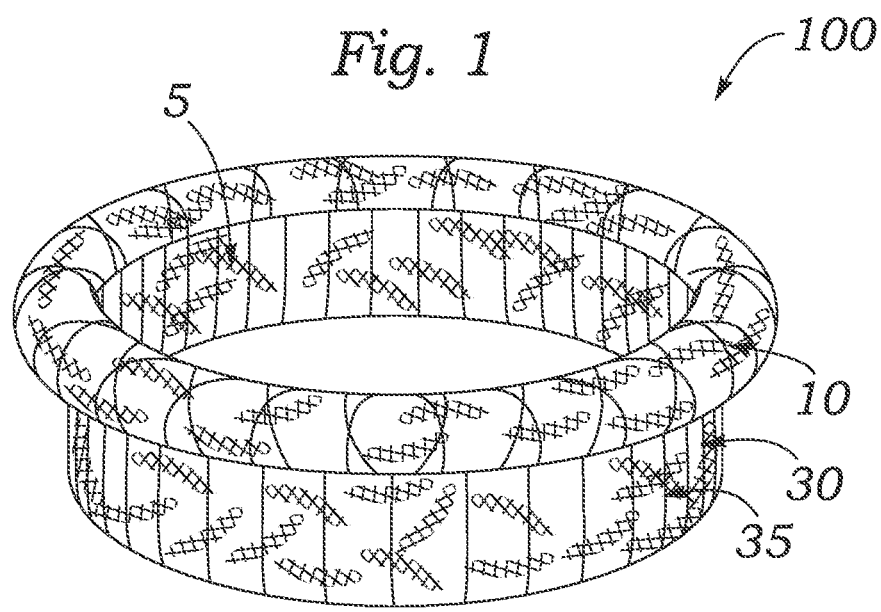
FIG. 1 is a perspective view of a docking device having three-dimensional (3D) woven fabric in accordance with one or more embodiments.

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding some embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

Certain docking devices and methods utilize a woven or knitted fabric skirt material. In some implementations, textile skirts are made by using polyethylene terephthalate (PET) in both warp and weft directions. However, generally, the PET material used may not have a shape memory effect that can change shape in connection with a trigger or stimulus, and may not be sufficiently elastic to provide for recovery after the deforming stress is removed. Therefore, it may be desirable to implement docking devices comprising fabrics and/or features that allow for improved flexibility with respect to shape or form. Some embodiments of docking devices disclosed herein are configured to adjust shape and/or form at least partially to the surrounding conditions/anatomy, and can take complex shapes to accommodate various different anatomies. In some implementations, the use of foam, polymer and/or biocompatible alloy with controlled diameter, size, and stiffness enables docking devices in accordance with the present disclosure to adjust and/or accommodate its shape or form to relatively complex anatomic geometries (e.g. different annulus sizes and/or shapes). That is, certain docking devices disclosed herein may be considered "universal" docking devices that provide desirable fit for a variety of sizes and/or shapes of patient anatomies.

Universal docking devices may be desired for use with certain implantable medical devices. For example, a universal docking device in accordance with the present disclosure may better conform to the complex anatomy associated with an implant site in some configurations. Furthermore, particularly with respect to bioprosthetic heart valves, universal docking devices in accordance with one or more embodiments of the present disclosure may help prevent paravalvular leakage and/or eliminate the need to carefully size the existing heart valves. With respect to these benefits, docking devices in accordance with one or more embodiments of the present disclosure can be configured to change shape and/or provide shape recovery after a deforming stress is removed, and can adjust to surrounding conditions to accommodate different complex anatomic geometries. Such attributes and/or characteristics can serve to at least partially mitigates paravalvular leakage.

Some embodiments disclosed herein provide a device that is configured and/or designed to improve the fit of an implantable bioprosthetic heart valve within a native valve annulus, which can advantageously at least partially mitigate issues associated with valve sizing and/or paravalvular leakage. For example, generally, the unique and/or irregular size and/or surface characteristics of native valve annuli can present challenges to providing an implantable bioprosthetic heart valve that fits within, and is provided in intimate contact or seal with, the valve annulus. To address such challenges, some embodiments disclosed herein advantageously provide a tubular or cylindrically-shaped device that is radially compressible for delivery and implantation in the native valve annulus before implantation of a bioprosthetic valve.

The structure of tubular or cylindrically-shaped devices in accordance with the present disclosure can comprise both an inner three-dimensional (3D) woven fabric and an outer covering of polymeric foam. For example, the 3D woven fabric can comprise three different fibers and/or yarns having different material properties. Different types of fibers and/or yarns that may be used can include shape memory material, such as Nitinol, low-melt thermoplastic polymer or resin having a melting point in the range of about 166-175° C., such as Nylon, and high-tenacity biocompatible material, such as PET. Furthermore, the polymeric foam can be attached to the outer surface of the 3D woven fabric and can provide a compressible seal with the native annulus.

In some implementations, docking devices in accordance with the present disclosure can be manufactured to the desired shape at least in part by pressing and/or heating the 3D woven fabric over a shape-setting mold at temperatures above the melting point of the low-melt thermoplastic polymer or resin. The melting of low-melt material can function as an adhesive to set the shape of the fabric. After the desired shape of the 3D woven fabric is set, a foam material can be attached or sewed onto the 3-D woven fabric.

In some implementations, the present disclosure provides a method for fabricating a universal docking device, wherein a main body of the docking device is made of shape memory material (e.g., Ni—Ti alloy, Nitinol) and thermoplastic fibers by utilizing 3D weaving techniques. Such 3D weaving techniques may be implemented on a specialized 3D weaving machine. For example, in some 3D weaving implementations in accordance with embodiments of the present disclosure, three sets of yarns are used to interlace with each other, as compared to two sets of yarn in flat-woven structures. The weave can be orthogonal or multilayer, and multiple layers can be woven together to form a 3D fabric. In the width-wise (i.e., "filling" or "weft") direction, memory metal (e.g., Ni—Ti) round wire and low-melt Nylon can be used apart from high tenacity polyethylene terephthalate (PET). The melting temperature of the low-melt nylon resin can be designed to be in range of 166-175° C.

After weaving the fabric, methods of fabricating a docking device in accordance with one or more embodiments of the present disclosure can involve pressing the fabric over a shape-setting mold (e.g., having a specific custom shape) and heated for a period of time (e.g., 30-60 min) at temperatures higher than the melting point of the low-melt Nylon resin, thereby causing the low-melt nylon to melt. The melted Nylon can act as an adhesive, and can at least partially set the shape of the fabric. The method may further involve leaving the shape-set fabric on the mold to cool-off for a period of time (e.g., 1 hour), and then removing the shape-set fabric and covering the same with a tubular woven fabric filled with foam or other at least partially compressible material (e.g., polymer, biocompatible alloy, etc.). The use of foam, polymer or biocompatible alloy outside the device can advantageously help reduce paravalvular leakage as such material can be compressed during delivery to the annulus, and once deployment is complete, the material can at least partially decompress and form an improved seal. The use of tubular textile around the form or other compressible material can help control the porosity of such materials, as foam or polymeric materials can be undesirably porous; the outside textile (e.g., PET) covering can reduce permeability.

Universal Docking Device

With reference now to FIG. 1 of the illustrative drawings, there is shown a universal docking device 100 in accordance with one or more embodiments. The docking device 100 includes a three-dimensional (3D) woven fabric 10 forming an internal surface 5, an outer surface 35, and having a thickness therebetween provided by the 3D nature of the fabric 10. In one embodiment, the 3D woven fabric can form a substantially hollow cylinder 30 having an outer surface 35 and inner surface 5. In some embodiments, the 3D woven fabric can form a ring, or ring-type form or structure. Other shapes are also possible, depending on the bioprosthetic device being docked within, or on, the docking device 100. In accordance with some implementations, the docking device 100 can be interposed between an implantable heart valve and a native valve annulus to provide an improved conforming fit and/or to reduce the likelihood and/or degree of a paravalvular leakage.

The 3D woven fabric 10 can be a hybrid fabric comprising polyethylene terephthalate (PET), memory metal (e.g., Ni—Ti alloy, Nitinol), and low-melt Nylon alloy, and can be made using any suitable or desirable weaving technique or configuration/arrangement. For example, in the width-wise (i.e., "weft," "filling") direction, memory metal (e.g., Ni—Ti) round wire and low-melt Nylon can be used apart from high-tenacity PET, or the memory metal wire can be used entirely the weft/filling direction in order to increase the shape memory effect of the fabric. The woven fabric structure 10 can be woven in 2D, 3D, and can be configured to fit any anatomical structure, by using the shape memory effect, or super elastic effect, of the memory metal wire or other material of the fabric. The woven fabric 10 can be configured to fit any desirable human anatomical part(s) through the use of shape memory alloy to change the shape of the mold. The fabric 10 can also be used in sheet form as a scaffold for tissue engineering with shape memory effect customized to any human anatomical shape.

In use, the docking device 100 can be compressed and delivered, such as through a catheter, to the implantation site. At the implantation site, the docking device 100 can be expanded to fit, and be held at, the local anatomy (e.g., the native heart valve annulus) associated with the implantation site. The docking device 100 can then act as a landing site for a bioprosthesis 200, such as a transcatheter heart valve.

Figure 2:
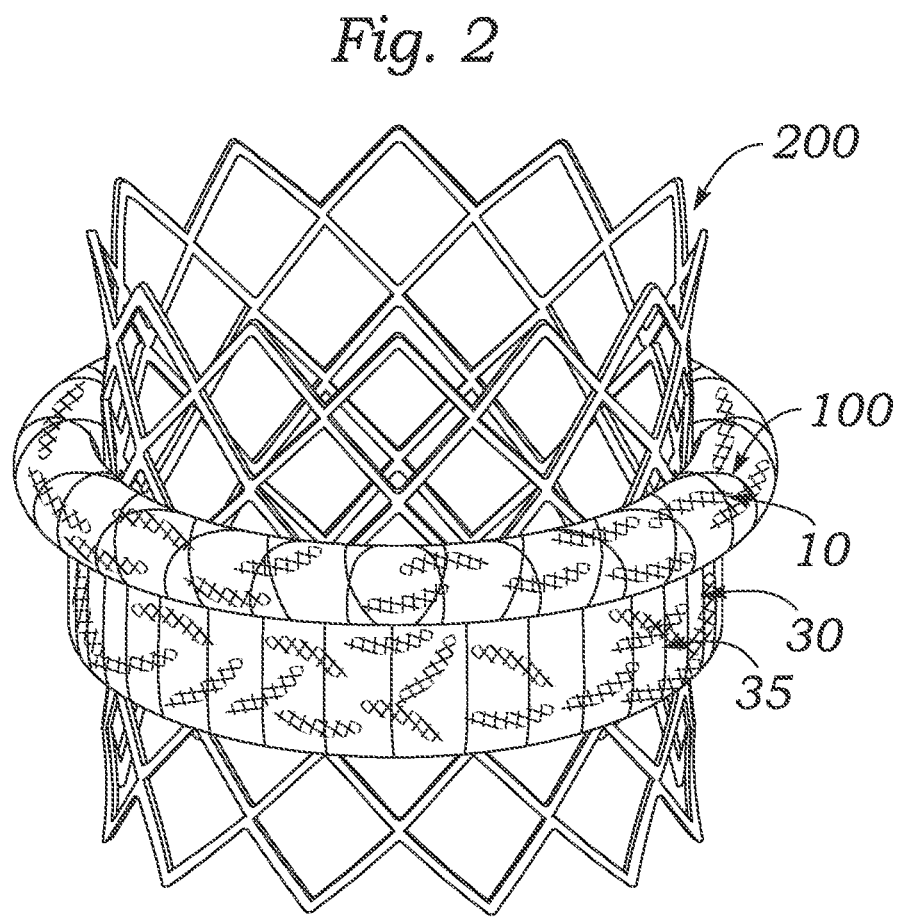
FIG. 2 is a perspective view of the frame of an exemplary transcatheter heart valve deployed inside the docking device of FIG. 1 in accordance with one or more embodiments.

FIG. 2 illustrates a perspective view of a frame 200 of an exemplary transcatheter heart valve deployed inside the docking device of FIG. 1 in accordance with one or more embodiments. With reference to FIG. 2, the docking device 100 can be interposed between a bioprosthesis 200, such as a transcatheter heart valve (THV), and native tissue, such as a native valve annulus (not shown). Although FIG. 2 only shows the frame of an exemplary transcatheter heart valve 200 within the docking device 100, it should be understood that, in some implementations, other devices besides a THV can benefit from implantation within the docking device 200 and/or other docking devices in accordance with embodiments of the present disclosure.

The docking device 100 can be configured or designed to be implanted at any suitable or desirable implantation site. However, implantation sites of different patients can present relative irregularity of shapes across patients. By using shape memory effect for the fabric 10, the docking device 100 can be used to fit into irregular shapes. The device 100 can be configured to be compressed and delivered through a catheter to the implant site. At the delivery site, depending on whether using super-elastic shape memory metal or polymer is used, the device 100 can expand by itself or through temperature stimulus to fit the size of the implantation site anatomy (e.g., heart valve annulus). Foam or other compressible material (not shown in FIGS. 1 and 2) disposed on the outside of the device 110 can also advantageously fill the open space between the implantation site anatomy (e.g., annulus) and the device 100 to create an effective sealing. The docking device 100 can act as a landing site for the prosthetic heart valve.

Figure 3A:
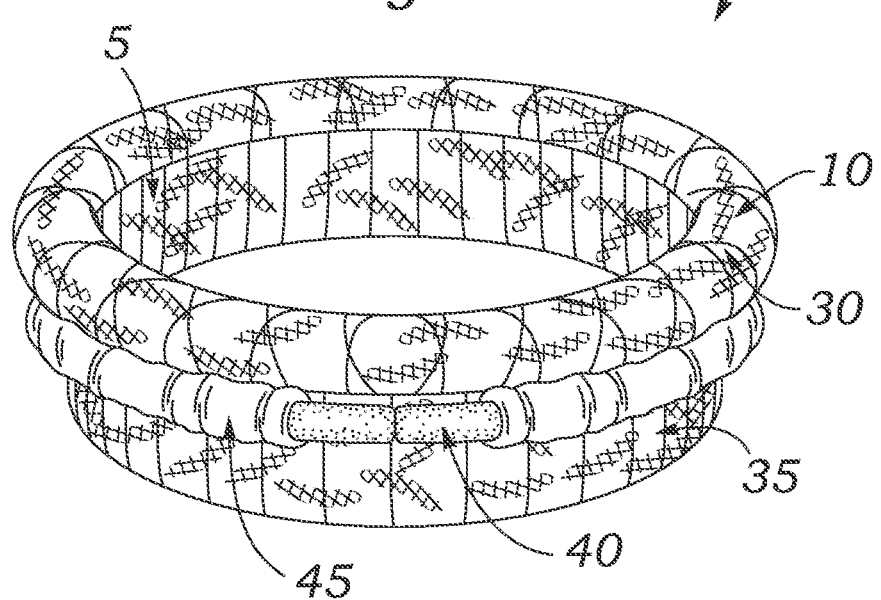
FIGS. 3A and 3B are perspective views of the docking device of FIG. 1, with a polymer foam coupled to an outer surface of the docking device and a tubular woven fabric covering the polymer foam in accordance with one or more embodiments.
Figure 3B:
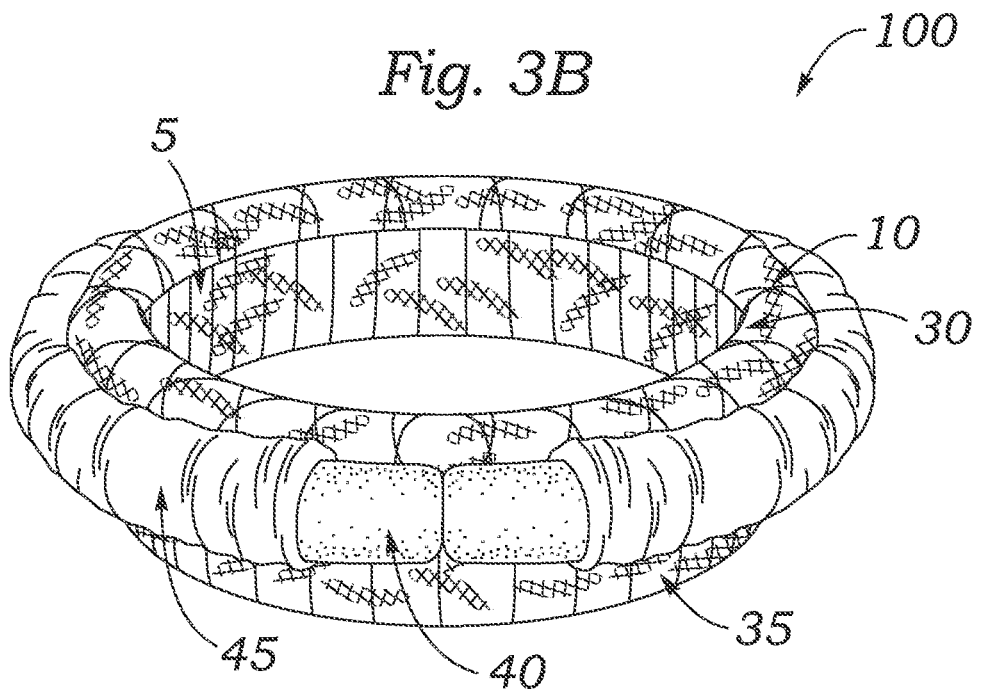

FIGS. 3A and 3B are perspective views of the docking device 100 of FIG. 1, wherein the docking device 100 has a polymer foam 40 coupled to an outer surface 35 of the docking device 100 and a tubular woven fabric 45 covering the polymer foam 40 in accordance with one or more embodiments. As shown in FIGS. 3A and 3B, the docking device 100 can further include a filler 40 (also referred to herein as a "filler structure") coupled to the outer surface 35 of the hollow cylinder 30. The filler 40 can comprise a polymeric foam. The polymeric foam can be an open-celled foam or a closed-cell foam. In some embodiments, the filler 40 form or structure can be provided to partially or completely surround a circumference of the outer surface 35 of the hollow cylinder 30. In some embodiments, the filler 40 can include a compressible or expandable material that can fill a desired space. In some embodiments, the filler 40 can be or comprise a polymer foam. In some embodiments, the filler 40 can comprise medical-grade silicone and/or a biocompatible alloy. In some embodiments, the filler can comprise one or more of polymeric foam, polyurethane foam, polyvinyl chloride foam, Styrofoam, polyimide foam, silicone foam, and/or microcellular foam.

In use, the filler structure 40 can be configured to be compressed during delivery of the docking device 100 to the implantation site (e.g., valve annulus). Once deployed, the filler 40 can be configured to decompress to provide a compressible seal against the surrounding native tissue. This compressible seal can be optimized by varying the shape, size, and stiffness of the filler 40. For example, the filler 40 can be configured, as shown in FIG. 3A, to cover a portion of the outer surface 35 of the hollow cylinder 30. Alternatively, the filler can be configured, as shown in FIG. 3B, to cover substantially all, or at least a majority, of the outer surface 35. In this way, the configuration of the filler 40 can be optimized to enable the docking device 100 to accommodate itself to complex anatomic geometries and/or, in the case of a prosthetic heart valve, to reduce paravalvular leakage.

In some embodiments, the filler 40 can be dimensioned to cover at least 10%, at least 20%, at least 30%, at least 40%, at least 50%, at least 60%, at least 70%, at least 80%, at least 90%, or 100% of the outer surface 35 of the hollow cylinder 30. In some embodiments, the filler can also be dimensioned to cover a percentage of the outer surface that includes and is between any two of the foregoing values.

FIG. 4 is a cutaway perspective view of a tubular woven fabric 45 covering a polymeric foam 40 in accordance with one or more embodiments. In some embodiments, the filler component/structure of a docking device in accordance with aspects of the present disclosure comprises a material that is, by itself, too porous to fully prevent or mitigate paravalvular leakage. Accordingly, with reference to FIG. 4, in some embodiments, the filler 40 can be covered with a tubular woven fabric 45, such as PET. In some embodiments, the filler 40 can be secured to a docking device, such as the docking device 100 shown in FIGS. 3A and 3B, by attaching the tubular woven fabric 45 to the outer surface 35 of the docking device's hollow cylinder 30. For example, the tubular woven fabric 45 may be attached to the outer surface 35 by adhering or suturing the tubular woven fabric 45 directly to the outer surface 35. So configured, the tubular woven fabric 45, with its low porosity and reduced permeability, can further mitigate paravalvular leakage. The tubular woven fabric 45 can also be provided to protect or ensure against the release of any undesired particulate matter from the filler 40, particularly with respect to embodiments in which the filler 40 is made of a porous and/or a foam material. Such particulate matter can be released due to the frictional forces imposed on the filler 40 during the delivery and/or implantation process(es). Release of such particulate matter can be undesirable as presenting a higher risk of embolization.

3D Woven Fabric

In some implementations, the present disclosure is related to relatively complex textile structures generated by utilizing weaving, braiding, knitting and/or a combination thereof. Such textiles structures can be generated using shape memory fibers or alloys (e.g., Nitinol) in combination with one or more thermoplastic textile fibers, such as Nylon, polyethylene terephthalate (PET), polypropylene (PP), and/or polybutylene terephthalate (PBT). Hybrid textile structures in accordance with the present disclosure can be created using a base substrate fabric, and using electrospinning to lay shape memory fibers on top of the substrate fabric, or by wrapping a low-melt Nylon in a core-sheath structure. As described above, the textile structure can be formed into a hollow cylinder form, wherein the outside of the cylinder form is at least partially enveloped by foam, polymer (e.g. medical-grade silicone), and/or a biocompatible alloy.

Devices in accordance with some implementations can include a three-dimensional (3D) woven fabric that is formed into a hollow cylinder, as well as a polymer foam attached to the hollow cylinder. The 3D woven fabric can advantageously comprise three different types of yarns or fibers, as described in detail herein. For example, the 3D woven fabric can comprise one or more of the following types of yarns and/or fibers: shape memory material, low-melt thermoplastic polymer or resin, and high-tenacity biocompatible material.

Example embodiments of 3D woven fabrics for use with docking devices are described below. As described above, 3D woven fabrics in accordance with embodiments of the present disclosure can comprise three different types of fibers or yarns. In some embodiments, the three different types of fibers or yarns can comprise a combination of a shape memory material, a low-melt thermoplastic polymer or resin, and a high-tenacity biocompatible material. In some embodiments, the shape memory material can be or comprise a metal alloy. The metal alloy can comprise nickel and/or titanium, such as Nitinol. In one embodiment, the shape memory material can provide the desired shape and geometry of the device.

With respect to the low-melt thermoplastic polymer or resin material, in some embodiments, such material can act as a binder or glue to fuse woven layers of the 3D fabric 10 together and conform the 3D woven fabric 10 to a desired shape. In some embodiments, the low-melt thermoplastic polymer or resin can be or comprise Nylon, for example.

The low-melt thermoplastic polymer or resin can have a relatively low-melting point. In accordance with an optional aspect, the low-melting point of the low-melt thermoplastic polymer or resin can be 200° C. or less, 195° C. or less, 190° C. or less, 185° C. or less, 180° C. or less, 175° C. or less, 170° C. or less, 165° C. or less, 160° C. or less, 155° C. or less, 150° C. or less, 145° C. or less, 140° C. or less, 135° C. or less, 130° C. or less, 125° C. or less, 120° C. or less, 115° C. or less, 110° C. or less, 105° C. or less, and 100° C. or less. The low-melting point can be within a range that includes and is between any two of the foregoing values.

With respect to the high-tenacity biocompatible material, such material can improve the durability of the 3D woven fabric 10 and promote tissue growth. In some embodiments, the high-tenacity biocompatible material can have a tenacity, or breaking load, of about 5 grams per Denier or more, about 6 grams per Denier or more, about 7 grams per Denier or more, about 8 grams per Denier or more, about 9 grams per Denier or more, about 10 grams per Denier or more, about 11 grams per Denier or more, about 12 grams per Denier or more, about 13 grams per Denier or more, about 14 grams per Denier or more, or about 15 grams per Denier. The breaking load can also be within a range that includes and/or is between any two of the foregoing values. In some embodiments, the high-tenacity biocompatible material can be PET.

In another embodiment, methods for making a docking device 100 for a bioprosthesis 200 are described. One such method comprises weaving a 3D woven fabric 10 by interlacing a shape memory material, a low-melt thermoplastic polymer or resin, and a high-tenacity biocompatible material. The shape memory material can be a metal alloy. The metal alloy can comprise nickel and titanium, such as Nitinol. The low-melt thermoplastic polymer or resin can be a polymer having a low-melting point. The polymer can be nylon. The high-tenacity biocompatible material can be PET.

3D woven fabrics can generally be woven by manipulating yarns in the length ("warp," or "ends"), width ("weft," "filling," or "picks"), and through-the-thickness directions. In some embodiments, the combination of the low-melt thermoplastic polymer and the 3D weave pattern can allow the thickness of the 3D woven fabric to be varied based on the number of layers of the weft and warp yarns. Thus, in one aspect, the thickness of the 3D woven fabric can be increased by increasing the number of layers of the weft and warp yarns with the low-melt thermoplastic polymer and the through-the-thickness yarns binding the plurality of layers together.

The through-the-thickness yarn can be incorporated at varying levels and angles within orthogonal (FIG. 5A), multilayer (FIG. 5B), and angle-interlock (FIG. 5C) woven structures to obtain desired mechanical properties. The weaving step can be performed on conventional weaving machines or specially-made weaving machines. In some embodiments, braiding or knitting techniques can be employed to manufacture the 3D fabric. However, in some implementations, such methods may not produce sufficient thickness.

Figure 5A:
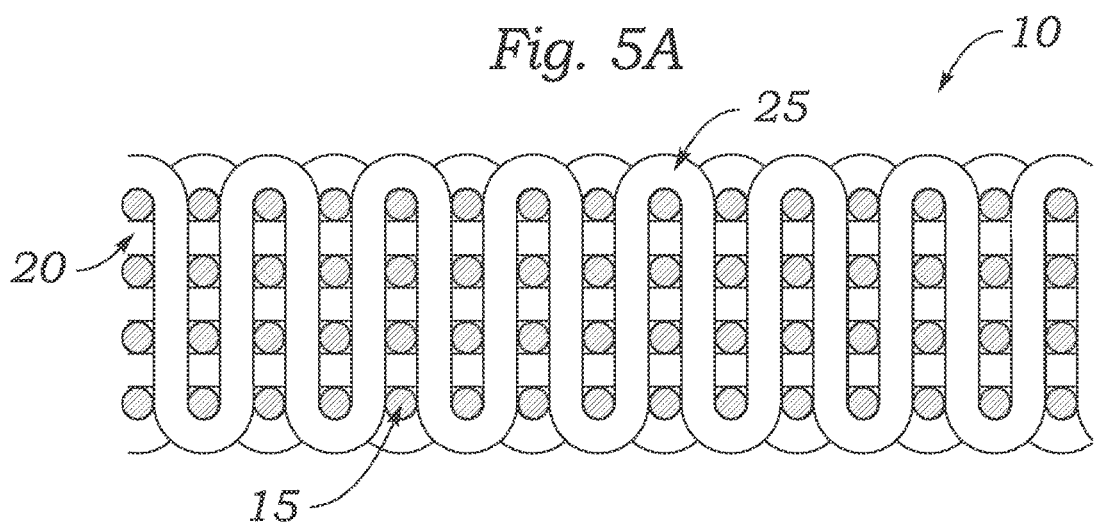
FIG. 5A is a cross-sectional schematic view of a 3D orthogonal woven unit cell in accordance with one or more embodiments.

With reference to FIG. 5A, in one embodiment, the 3D woven fabric 10 can comprise an orthogonal weave structure. Orthogonal weave structures can include a set of warp yarns 15, a set of filling yarns 20, and a set of through-the-thickness yarns 25. Warp yarns 15 can be placed in the fabric length direction and filling yarns 20 can be inserted between the length layers to form double picks. Through-the-thickness yarns 25 can interconnect the other two yarn sets and provide structural integrity. The thickness of the orthogonal structure can be formed by the number of layers of the warp or weft yarn. In some embodiments, yarns are substantially straight in the warp, weft, and through-the-thickness directions. The through-the-thickness yarns can generally travel vertically between the top and bottom weft yarn layers, and can also interlink with weft yarn layers at other levels in some embodiments.

In some embodiments, the 3D woven fabric 10 can comprise an orthogonal weave structure, wherein the set of warp yarns 15 can comprise a shape memory material, the set of filling yarns 20 can comprise a low-melt thermoplastic polymer or resin, and the set of through-the-thickness yarns 25 can comprise a high-tenacity biocompatible material.

In some embodiments, the 3D woven fabric 10 can comprise an orthogonal weave structure, wherein the set of warp yarns 15 can comprise a high-tenacity biocompatible material, the set of filling yarns 20 can comprise a shape memory material, and the set of through-the-thickness yarns 25 can comprise a low-melt thermoplastic polymer or resin.

Figure 5B:
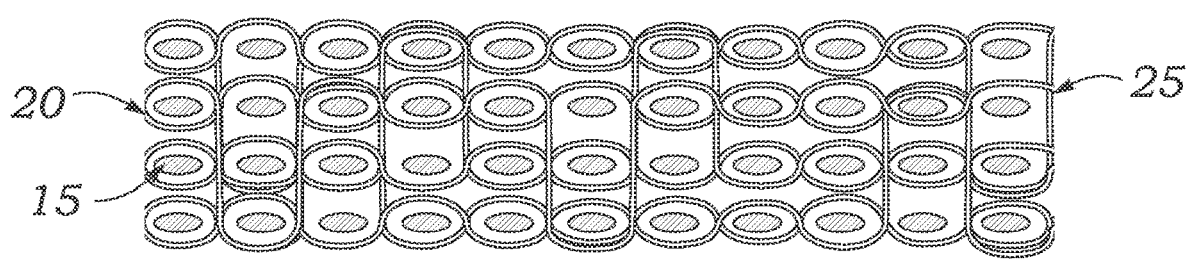
FIG. 5B is a cross-sectional schematic view of a 3D multilayer woven unit cell in accordance with one or more embodiments.

With reference to FIG. 5B, in some embodiments, the 3D woven fabric 10 can comprise a multilayer weave structure. Multilayer weave structures can include a set of warp yarns 15, a set of weft yarns 20, and a set of through-the-thickness binding yarns 25. Warp yarns 15 can be interlaced with weft yarns 20 at each layer according to the weave pattern in in-plane principal directions, whereas binding yarns 25 can be interlaced with warp yarns 15 at each layer according to the weave pattern in out-of-plane principal directions. The multilayer weave structure can be fully interlaced or semi-interlaced.

In some embodiments, the 3D woven fabric 10 can comprise a multilayer weave structure, wherein the set of warp yarns 15 can comprise a shape memory material, the set of weft yarns 20 can comprise a low-melt thermoplastic polymer or resin, and the set of binding yarns 25 can comprise a high-tenacity biocompatible material.

In some embodiments, the 3D woven fabric 10 can comprise a multilayer weave structure, wherein the set of warp yarns 15 can comprise a high-tenacity biocompatible material, the set of weft yarns 20 can comprise a shape memory material, and the set of binding yarns 25 can comprise a low-melt thermoplastic polymer or resin.

Figure 5C:
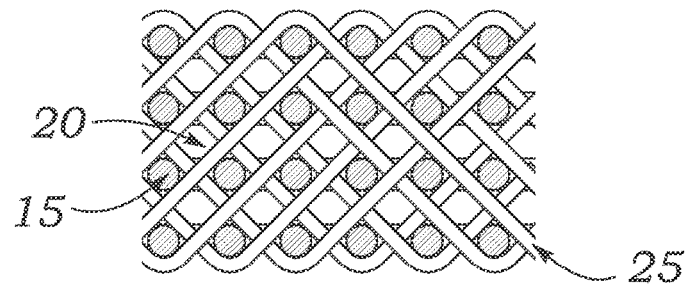
FIG. 5C is a cross-sectional schematic view of a 3D angle-interlock woven unit cell in accordance with one or more embodiments.

With reference to FIG. 5C, in some embodiments, the 3D woven fabric 10 comprises an angle-interlock weave structure. Angle-interlock weave structures in accordance with the present disclosure can include a set of warp yarns 15, a set of straight weft yarns 20 (wadding), and a set of bias weft yarns 25 that weave with the warp yarns 15 in a diagonal direction in the thickness. In layer-to-layer angle-interlock weaves (not shown), bias weft yarns 25 can travel between two or more successive layers making interlacements with several wadding yarns 20 according to the weave pattern. In through-thickness angle-interlock weaves (FIG. 5C), bias weft yarns 25 can bind diagonally from the top layer to the bottom layer.

In some embodiments, the 3D woven fabric 10 can comprise an angle-interlock structure, wherein the set of warp yarns 15 can comprise a shape memory material, the set of straight weft yarns 20 can comprise a low-melt thermoplastic polymer or resin, and the set of bias weft yarns 25 can comprise a high-tenacity biocompatible material.

In some embodiments, the 3D woven fabric 10 can comprise an angle-interlock structure, wherein the set of warp yarns 15 can comprise a high-tenacity biocompatible material, the set of straight weft yarns 20 can comprise a shape memory material, and the set of bias weft yarns 25 can comprise a low-melt thermoplastic polymer or resin.

It should be understood that other varieties of 3D weave structures, including different varieties of orthogonal, multilayer, and angle-interlock weave structures, may be used in connection with embodiments of the present disclosure. To optimize the physical characteristics of the docking device 100 for use with a particular bioprosthesis 200 or installation site, the 3D woven fabric 10 can be manufactured using any of the different varieties of 3D weave structures.

For example, in use with a bioprosthetic heart valve, the docking device 100 may be subjected to compressive forces between the bioprosthesis 200 and the surrounding native valve tissue. The compressibility of the docking device 100 can be, in part, a function of the compressibility of the 3D woven fabric, which can, in turn, be a function of the fabric's weave structure, fabric density, and/or other characteristics of the constituent fibers/yarns. Accordingly, the 3D woven fabric's 10 weave structure and fabric density can be selected to optimize the compressibility of docking device 100.

Fabric density can be quantified by ends-per-inch (EPI) and/or picks-per-inch (PPI). In some embodiments, the 3D woven fabric 10 can have about 115 EPI, about 120 EPI, about 125 EPI, about 130 EPI, about 135 EPI, about 140 EPI, about 145 EPI, about 150 EPI, about 155 EPI, about 160 EPI, about 165 EPI, about 170 EPI, about 175 EPI, about 180 EPI, about 185 EPI, about 190 EPI, about 195 EPI, about 200 EPI, about 205 EPI, about 210 EPI, about 215 EPI, about 220 EPI, about 225 EPI, about 230 EPI, about 235 EPI, about 240 EPI, about 245 EPI, about 250 EPI, about 255 EPI, about 260 EPI, about 265 EPI, about 270 EPI, about 275 EPI, about 280 EPI, about 285 EPI, about 290 EPI, about 295 EPI, about 300 EPI, about 305 EPI, about 310 EPI, about 315 EPI, about 320 EPI, about 325 EPI, about 330 EPI, about 335 EPI, about 340 EPI, about 345 EPI, or about 350 EPI. In some embodiments, the 3D woven fabric 10 can have ends-per-inch between and including any two of the foregoing values.

In one embodiment, the 3D woven fabric 10 can have about 115 PPI, about 120 PPI, about 125 PPI, about 130 PPI, about 135 PPI, about 140 PPI, about 145 PPI, about 150 PPI, about 155 PPI, about 160 PPI, about 165 PPI, about 170 PPI, about 175 PPI, about 180 PPI, about 185 PPI, about 190 PPI, about 195 PPI, about 200 PPI, about 205 PPI, about 210 PPI, about 215 PPI, about 220 PPI, about 225 PPI, about 230 PPI, about 235 PPI, about 240 PPI, about 245 PPI, about 250 PPI, about 255 PPI, about 260 PPI, about 265 PPI, about 270 PPI, about 275 PPI, about 280 PPI, about 285 PPI, about 290 PPI, about 295 PPI, about 300 PPI, about 305 PPI, about 310 PPI, or about 315 PPI, about 320 PPI, about 325 PPI, about 330 PPI, about 335 PPI, about 340 PPI, about 345 PPI, or about 350 PPI. In some embodiments, the 3D woven fabric 10 can have picks-per-inch between and including any two of the foregoing values.

In some embodiments, the docking device 100 exhibits a compressibility of no more than 5%, no more than 10%, no more than 15%, no more than 20%, no more than 25%, no more than 30%, no more than 35%, no more than 40%, no more than 45%, no more than 50%, no more than 55%, no more than 60%, no more than 65%, or no more than 70% across its thickness. In some embodiments, the docking device can exhibit a compressibility of between and including any two of the foregoing values.

Figure 6:
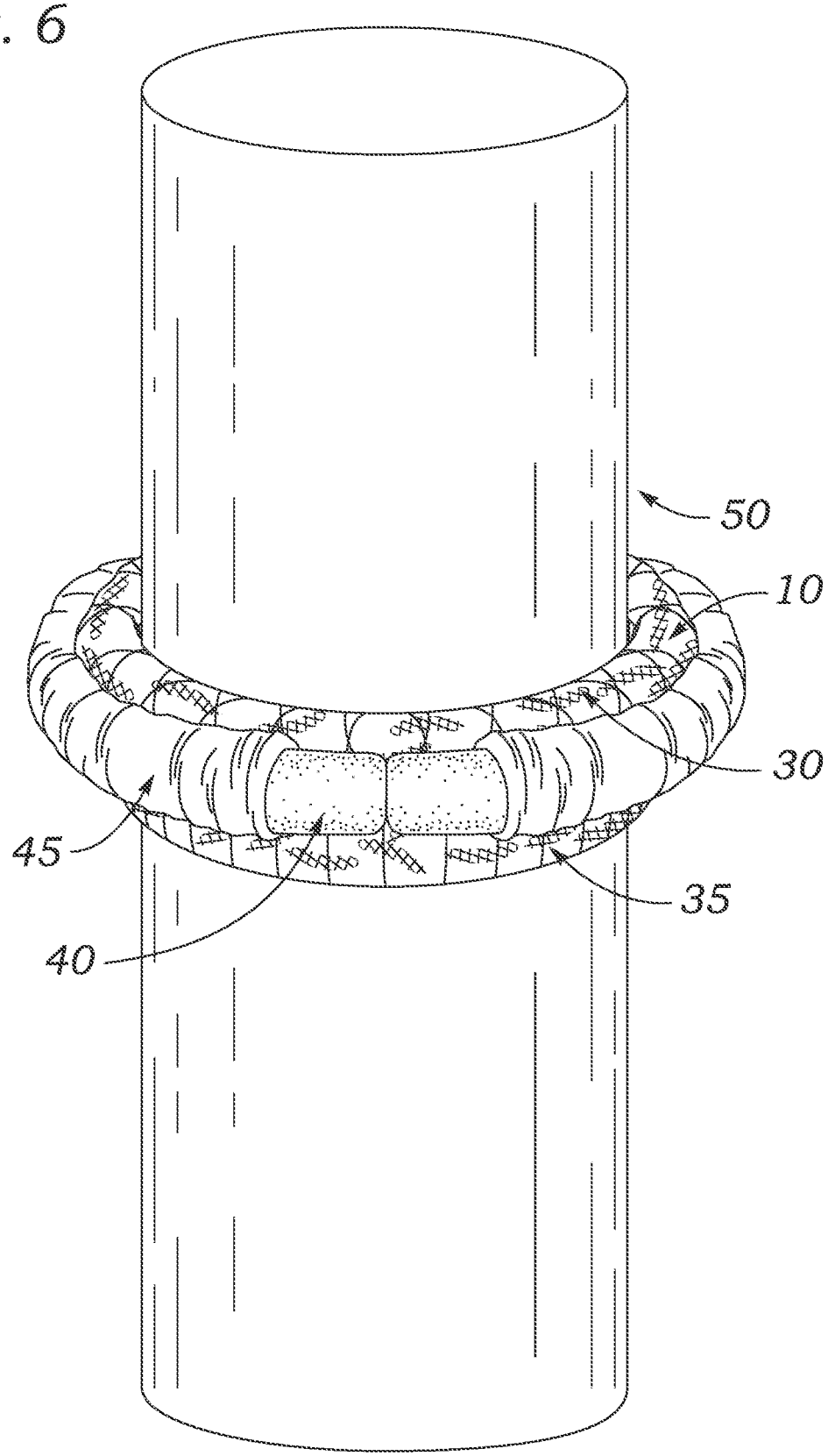
FIG. 6 is a perspective view of the docking device of FIG. 1 in a shape setting mandrel in accordance with one or more embodiments.

With reference to FIG. 6, a method for making a docking device 100 for a bioprosthesis can comprise the step of pressing and heating the 3D woven fabric 10 over a shape-setting mold 50 at temperatures greater than the melting point of the low-melt thermoplastic polymer or resin. This step can melt the low-melt thermoplastic polymer or resin yarn, which can function as an adhesive to set the shape of the 3D woven fabric 10 as desired. In some embodiments, the 3D woven fabric 10 can be heated on the shape-setting mold 50 from about 30 minutes to about 60 minutes. In some embodiments, the bioprosthesis can be a transcatheter heart valve, and the 3D woven fabric 10 can be molded accordingly. It should be understood, however, that the 3D woven fabric 10 can be molded to accommodate other bioprostheses, or as a scaffold for tissue engineering.

In some embodiments, the method can further comprise the step of attaching a filler 40 to a surface 35 of the 3D woven fabric 10, for example by sewing the filler 40 to the surface 35 of the 3D woven fabric 10. In a further embodiment, the method can include the step of covering the filler 40 with a tubular woven fabric 45 comprising, for example, polyethylene terephthalate (PET). In some embodiments, the filler 40 can be a polymer foam.

It should be appreciated from the foregoing description that the present invention provides a universal docking device that can be radially compressible, for delivery and implantation, and that changes shape and recovers after a deforming stress is removed. The docking device adjusts to surrounding conditions to accommodate different complex anatomic geometries, and provides conforming support while minimizing or eliminating leakage around the implanted device.

The invention has been described in detail with reference only to the presently preferred embodiments. Persons skilled in the art will appreciate that various modifications can be made without departing from the invention. Accordingly, the invention is defined only by the following claims.

ADDITIONAL EMBODIMENTS

Depending on the embodiment, certain acts, events, or functions of any of the processes described herein can be performed in a different sequence, may be added, merged, or left out altogether. Thus, in some embodiments, not all described acts or events are necessary for the practice of the processes. Moreover, in some embodiments, acts or events may be performed concurrently.

Conditional language used herein, such as, among others, "can," "could," "might," "may," "e.g.," and the like, unless specifically stated otherwise, or otherwise understood within the context as used, is intended in its ordinary sense and is generally intended to convey that some embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that some embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A docking device comprising:
   a hollow cylindrical body portion having an internal surface and an outer surface;
   wherein:
   the hollow cylindrical body portion is formed of a three-dimensional (3D) woven fabric comprising a multilayer weave structure including a set of warp yarns of a first type of fiber, a set of weft yarns of a second type of fiber, and a set of through-the-thickness binding yarns of a third type of fiber;
   the first type of fiber comprises a first one of a group of different fibers consisting of shape memory metal, low-melt thermoplastic polymer or resin, and high-tenacity biocompatible material;
   the second type of fiber comprises a second different one of the group; and
   the third type of fiber comprises a third different one of the group.

2. The docking device of claim 1, wherein the 3D woven fabric has an orthogonal weave structure.

3. The docking device of claim 2, wherein:
   the warp yarns are arranged in a fabric length direction;
   the weft yarns are filing fibers inserted between length layers of the warp yarns; and
   the through-the-thickness binding yarns interconnect layers of the weft yarns.

4. The docking device of claim 3, wherein:
   the first type of fiber is the high-tenacity biocompatible material;
   the second type of fiber is the shape memory metal; and
   the third type of fiber is the low-melt thermoplastic polymer or resin.

5. The docking device of claim 4, wherein:
   the high-tenacity biocompatible material comprises polyethylene terephthalate (PET) and is configured to provide durability and promote tissue growth for the 3D woven fabric;

the shape memory metal comprises nickel titanium alloy; and the low-melt thermoplastic polymer or resin comprises nylon and is configured to fuse woven layers of the 3D woven fabric together.

6. The docking device of claim 1, wherein:
the warp yarns are interlaced with layers of the weft yarns in in-plane principal directions; and
the through-the-thickness binding yarns are interlaced with layers of the warp yarns in out-of-plane principal directions.

7. The docking device of claim 6, wherein:
the first type of fiber is the shape memory metal;
the second type of fiber is the low-melt thermoplastic polymer or resin; and
the third type of fiber is the high-tenacity biocompatible material.

8. The docking device of claim 6, wherein:
the first type of fiber is the high-tenacity biocompatible material;
the second type of fiber is the shape memory metal; and
the third type of fiber is the low-melt thermoplastic polymer or resin.

9. The docking device of claim 1, wherein the 3D woven fabric has an angle-interlock weave structure.

10. The docking device of claim 9, wherein:
the weft yarns comprise straight weft wadding yarns; and
the through-the-thickness binding yarns comprise bias weft yarns that weave with the warp yarns in a diagonal direction in a thickness of the 3D woven fabric.

11. The docking device of claim 10, wherein:
the first type of fiber is the shape memory metal;
the second type of fiber is the low-melt thermoplastic polymer or resin type of fiber; and
the third type of fiber is the high-tenacity biocompatible material.

12. The docking device of claim 10, wherein:
the first type of fiber is the high-tenacity biocompatible material;
the second type of fiber is the shape memory metal; and
the third type of fiber is the low-melt thermoplastic polymer or resin.

13. The docking device of claim 1, further comprising:
an elongate filler structure wrapped at least partially around a circumference of the outer surface of the hollow cylindrical body portion; and
a tubular woven fabric disposed around the elongate filler structure over a length of the elongate filler structure.

14. The docking device of claim 13, wherein:
the elongate filler structure comprises foam; and
the tubular woven fabric is less porous than the elongate filler structure.

15. The docking device of claim 13, wherein the tubular woven fabric is attached to the outer surface of the hollow cylindrical body portion.

16. The docking device of claim 13, further comprising a ring formed of the 3D woven fabric at an axial end of the hollow cylindrical body portion, wherein the tubular woven fabric is attached to the hollow cylindrical body portion adjacent to the ring.

17. The docking device of claim 14, wherein the foam is one of the group consisting of polymeric foam, polyurethane foam, polyvinyl chloride foam, polyimide foam, and microcellular foam.

18. The docking device of claim 13, wherein the elongate filler structure comprises silicone.

19. The docking device of claim 13, wherein ends of the elongate filler structure are exposed past ends of the tubular woven fabric.

20. The docking device of claim 1, wherein the high-tenacity biocompatible material comprises polyethylene terephthalate (PET).

21. The docking device of claim 1, wherein the shape memory metal comprises nickel titanium alloy.

22. The docking device of claim 1, wherein the low-melt thermoplastic polymer or resin comprises nylon.

* * * * *